US010821220B2

(12) United States Patent
Murphy et al.

(10) Patent No.: US 10,821,220 B2
(45) Date of Patent: Nov. 3, 2020

(54) CONTINUOUS FLOW SEPARATION CHAMBER WITH OPTICAL SENSOR

(71) Applicant: Haemonetics Corporation, Boston, MA (US)

(72) Inventors: Matthew Murphy, Marshfield, MA (US); Dominique Uhlmann, Abington, MA (US); Edward Powers, Hampton Falls, NH (US); Michael Ragusa, Hingham, MA (US); Etienne Pagès, Cessy (FR)

(73) Assignee: Haemonetics Corporation, Boston, MA (US)

( * ) Notice: Subject to any disclaimer, the term of this patent is extended or adjusted under 35 U.S.C. 154(b) by 0 days.

(21) Appl. No.: 16/379,086

(22) Filed: Apr. 9, 2019

(65) Prior Publication Data

US 2019/0231965 A1    Aug. 1, 2019

Related U.S. Application Data

(62) Division of application No. 14/072,220, filed on Nov. 5, 2013, now Pat. No. 10,293,097.

(Continued)

(51) Int. Cl.
*A61M 1/36* (2006.01)
*B04B 5/04* (2006.01)
*B04B 13/00* (2006.01)

(52) U.S. Cl.
CPC ........ *A61M 1/3693* (2013.01); *A61M 1/3696* (2014.02); *B04B 5/0442* (2013.01);
(Continued)

(58) Field of Classification Search
CPC .............. A61M 1/3693; A61M 1/3696; A61M 2205/3306; B04B 5/0442; B04B 2013/006; B04B 2005/0464
(Continued)

(56) References Cited

U.S. PATENT DOCUMENTS 3,145,713 A    8/1964  Latham, Jr.
3,955,755 A    5/1976  Breillatt, Jr. et al.
(Continued)

FOREIGN PATENT DOCUMENTS

CN    2927990 Y    8/2007
CN    102046224 A    5/2011
(Continued)

OTHER PUBLICATIONS

U.S. Appl. No. 14/072,220, filed Nov. 5, 2013, 2014-0128239.

*Primary Examiner* — Walter D. Griffin
*Assistant Examiner* — Shuyi S. Liu
(74) *Attorney, Agent, or Firm* — McCarter & English, LLP; Jonathan C. Lovely

(57) ABSTRACT

A continuous flow centrifuge bowl includes a rotatable outer body, and a top and bottom core that are rotatable with the outer body. The bottom core has a wall extending proximally from a bottom wall. The proximally extending wall is radially outward from at least a portion of the top core and, together with the top core, defines a primary separation region in which initial separation of the whole blood occurs. The bowl may also have a secondary separation region located between the top core and the outer body, and a rotary seal that couples an inlet port and two outlet ports to the outer body. The inlet port may be connected to an inlet tube that extends distally into a whole blood introduction region. Additionally, one of the outlet ports may be connected to an extraction tube that extends into a region below the bottom core.

17 Claims, 7 Drawing Sheets

Related U.S. Application Data

(60) Provisional application No. 61/722,506, filed on Nov. 5, 2012.

(52) U.S. Cl.
CPC ............... *A61M 2205/3306* (2013.01); *B04B 2005/0464* (2013.01); *B04B 2013/006* (2013.01)

(58) Field of Classification Search
USPC ...... 494/1, 2, 3, 7, 10, 38, 40, 56, 76, 77, 84
See application file for complete search history.

(56) References Cited

U.S. PATENT DOCUMENTS

| | | | |
|---|---|---|---|
| 4,300,717 A | 11/1981 | Latham, Jr. | |
| 4,710,161 A | 12/1987 | Takabayashi et al. | |
| 4,729,759 A * | 3/1988 | Krook | B04B 1/08 |
| | | | 494/4 |
| 4,859,333 A | 8/1989 | Panzani | |
| 4,879,031 A | 11/1989 | Panzani | |
| 4,943,273 A | 7/1990 | Pages | |
| 4,983,158 A | 1/1991 | Headley | |
| 5,464,536 A * | 11/1995 | Rogers | B01D 17/0217 |
| | | | 210/380.1 |
| 5,478,479 A | 12/1995 | Herrig | |
| 5,514,070 A | 5/1996 | Pages | |
| 5,651,766 A | 7/1997 | Kingsley et al. | |
| 5,720,921 A | 2/1998 | Meserol | |
| 5,779,660 A | 7/1998 | Kingsley et al. | |
| 5,853,382 A | 12/1998 | Kingsley et al. | |
| 5,882,289 A | 3/1999 | Sakota et al. | |
| 6,099,491 A | 8/2000 | Headley et al. | |
| 6,224,531 B1 * | 5/2001 | Frehland | B04B 5/005 |
| | | | 494/49 |
| 6,743,192 B1 * | 6/2004 | Sakota | A61M 1/3693 |
| | | | 210/195.1 |
| 7,037,428 B1 | 5/2006 | Robinson et al. | |
| 7,582,049 B2 | 9/2009 | Hlavinka et al. | |
| 8,070,664 B2 | 12/2011 | Rochat | |
| 2001/0006810 A1 | 7/2001 | Brown | |
| 2002/0058030 A1 | 5/2002 | Monroy et al. | |
| 2003/0125881 A1 | 7/2003 | Ryan | |
| 2003/0181305 A1 * | 9/2003 | Briggs | A61M 1/3693 |
| | | | 494/37 |
| 2003/0233064 A1 | 12/2003 | Arm et al. | |
| 2004/0127840 A1 | 7/2004 | Gara et al. | |
| 2006/0226090 A1 * | 10/2006 | Robinson | A61M 1/3693 |
| | | | 210/787 |
| 2007/0012623 A1 | 1/2007 | Robinson et al. | |
| 2009/0259163 A1 | 10/2009 | Pages et al. | |
| 2009/0259164 A1 | 10/2009 | Pages et al. | |
| 2013/0310241 A1 | 11/2013 | Kabaha et al. | |
| 2014/0045672 A1 * | 2/2014 | Galavotti | B04B 5/0442 |
| | | | 494/44 |
| 2014/0128239 A1 | 5/2014 | Murphy et al. | |
| 2015/0273132 A1 | 10/2015 | Ragusa et al. | |

FOREIGN PATENT DOCUMENTS

| | | | | |
|---|---|---|---|---|
| GB | 480216 A | * | 2/1938 | ............... B04B 1/08 |
| GB | 480216 A | | 2/1938 | |
| JP | 9-104631 A | | 4/1997 | |
| JP | 9-192215 A | | 7/1997 | |
| JP | 3021334 B2 | | 3/2000 | |
| JP | 2000-102603 A | | 4/2000 | |
| JP | 2006-020756 A | | 1/2006 | |
| RU | 2534631 C1 | | 12/2014 | |
| WO | 2009/129131 A1 | | 10/2009 | |
| WO | 2012/137086 A1 | | 10/2012 | |
| WO | 2014/070209 A1 | | 5/2014 | |

\* cited by examiner

CONTINUOUS FLOW SEPARATION CHAMBER WITH OPTICAL SENSOR

PRIORITY

This patent application is a divisional of and claims priority from U.S. patent application Ser. No. 14/072,220, filed Nov. 5, 2013, entitled, "Continuous Flow Separation Chamber With Weir Disk," and naming Matthew Murphy, Dominique Uhlmann, Edward Powers, Michael Ragusa, and Etienne Pages as inventors, the disclosure of which is incorporated herein, in its entirety, by reference.

U.S. patent application Ser. No. 14/072,220, in turn, claims priority from U.S. Provisional Patent Application No. 61/722,506, filed Nov. 5, 2012, entitled, "Continuous Flow Separation Chamber," and naming Matthew Murphy, Dominique Uhlmann, Edward Powers, Michael Ragusa, and Etienne Pages as inventors, the disclosure of which is incorporated herein, in its entirety, by reference.

TECHNICAL FIELD

The present invention relates to whole blood separation chambers, and more particularly to continuous flow separation chambers and methods of using the same.

BACKGROUND ART

Apheresis is a procedure in which individual blood components can be separated and collected from whole blood withdrawn from a subject. Typically, whole blood is withdrawn through a needle inserted into a vein of the subject's arm and into a cell separator, such as a centrifugal bowl. Once the whole blood is separated into its various components, one or more of the components can be removed from the centrifugal bowl. The remaining components can be returned to the subject. In some instances, the remaining components can be returned along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Blood components separated may include, for example, a high density component such as red blood cells, an intermediate density component such as platelets or white blood cells, and a lower density component such as plasma.

As mentioned above, many prior art apheresis systems use a centrifuge bowl to separate and collect the individual blood components. In such systems, the whole blood is drawn into the bowl and separated into the various components (e.g., within a separation region). As the bowl continues to fill with whole blood, red blood cells sediment towards the outer diameter of the bowl, causing a plasma interface (e.g., the interface between the red blood cells and plasma) to move towards the center of the bowl. When the plasma interface reaches a certain point, plasma is pushed out of the bowl and may be collected in one or more collection bags. Blood will continue to fill the bowl until the plasma interface reaches a certain position. At this point, the introduction of whole blood into the bowl is stopped.

After the introduction of whole blood is stopped, the collected plasma may be recirculated to the bowl in order to remove a layer of platelets formed within the bowl. Once the platelets are collected, many prior art systems then collect and/or return the remaining contents of the bowl to the patient. The process is then repeated in a batch-like/intermittent manner until a target amount of blood component (e.g., red blood cells, platelets, plasma, etc.) is collected.

SUMMARY OF THE EMBODIMENTS

In accordance with one embodiment of the present invention, a centrifuge bowl for continuous separation of whole blood (e.g., into red blood cells and plasma) may include an outer body rotatable about a longitudinal axis of the centrifuge bowl. Within the outer body, the bowl can have a top core and a bottom core. The top core may be rotatable and coaxial with the outer body. The bottom core may have a bottom wall and a proximally extending wall that extends from the bottom wall and is radially outward from at least a portion of the top core. The proximally extending wall and a portion of the top core can define a primary separation region in which separation of the whole blood begins. The bowl may also have a secondary separation region located between the top core and the outer body.

In some embodiments, the bowl may have an inlet port for introducing whole blood into the centrifuge bowl, and an inlet tube fluidly connected to and extending distally from the inlet port. The inlet tube may introduce the whole blood into an introduction region (between the top core and the bottom core). Additionally, the bowl can have a first blood component outlet port and a second blood component outlet port. The first blood component outlet port may be for drawing a first blood component out of the centrifuge bowl. A first blood component extraction tube may extend from the first blood component outlet port and through the bottom core to a region below the bottom core. The second blood component outlet port may be fluidly connected to the secondary separation region and may be configured to allow a second blood component to exit the centrifuge bowl. A centrifuge bowl rotary seal may be attached to the outer body and couple the inlet port, first blood component outlet port, and second blood component outlet port to the outer body.

The primary separation region may be fluidly connected to the secondary separation region, and there may be a first blood component extraction region located between the bottom wall of the bottom core and a bottom of the outer body. The first blood component extraction tube may extend into the first blood component extraction region. Additionally, the proximally extending wall may be configured to prevent whole blood from entering the first blood component extraction region. The bowl may also include a fluid path way that (1) extends from the introduction region to the primary separation region, (2) fluidly connects the inlet tube and the primary separation region, and (3) is located between the bottom wall of the top core and the upper surface of the bottom core.

The bowl may also include a seal located between the first blood component extraction tube and the bottom core, and a bypass seal (e.g., a rotary seal). The top core may include a chimney extending through the top core along the longitudinal axis of the centrifugal bowl. The inlet tube and first blood component extraction tube may extend through the chimney. The bypass seal may be located between the outer diameter of the inlet tube and the inner diameter of the chimney, and may isolate the introduction region from the chimney. The first blood component extraction tube may be coaxial with the inlet tube.

On a shoulder of the bowl/outer body, the bowl may have an optical sensor that monitors an interface between the first blood component and the second blood component. The optical sensor may control the operation of a first blood component pump based upon a location of the interface. The first blood component pump may draw the first blood component from the bowl.

The bowl may also have a weir disk extending inward from a neck portion of the outer body. The second blood component may flow over the weir disk into the neck portion of the outer body prior to exiting the centrifuge bowl via the second blood component outlet port. The bottom surface of the weir disk and a top surface of the top core may define a second blood component channel that fluidly connects the secondary separation region and the second blood component outlet port.

In accordance with further embodiments, a centrifuge bowl for continuous separation of whole blood may include an outer body that is rotatable about a longitudinal axis of the centrifuge bowl, a top core, and a separation region. The top core may be located within and may be rotatable with the outer body. The top core may also be coaxial with the outer body and have a chimney extending through it along the longitudinal axis of the centrifuge bowl. The separation region may be located between the top core and the outer body, and rotation of the centrifuge bowl may separate the whole blood within the separation region into a first blood component (e.g., red blood cells) and a second blood component (e.g., plasma).

The centrifuge bowl may also have an inlet port for introducing whole blood into the centrifuge bowl. The inlet port may be fluidly connected to an inlet tube that extends distally from the inlet port and through the chimney. The inlet tube may introduce the whole blood into an introduction region. There may be a bypass seal (e.g., a rotary seal) between an outer diameter of the inlet tube and an inner diameter of the chimney to isolate the introduction region from the chimney. A first blood component outlet port (e.g., in fluid communication with the separation region) may be used to draw the first blood component out of the centrifuge bowl. A first blood component extraction tube may be coaxial with the inlet tube and extend from the first blood component outlet port to a first blood component extraction region. Additionally, the bowl may include a second blood component outlet port fluidly connected to the separation region and configured to draw a second blood component from the centrifuge bowl. A centrifuge bowl rotary seal attached to the outer body may couple the inlet port, first blood component outlet port, and second blood component outlet port to the outer body.

In addition to the top core, in some embodiments, the bowl may also include a bottom core located within and rotatable with the outer body. The bottom core may be located between the bottom surface of the outer body and the top core. The first blood component extraction region may be located between the bottom wall of the bottom core and a bottom of the outer body, and may fluidly connect the first blood component extraction tube and the separation region. The first blood component extraction tube may extend through the bottom core and into the first blood component extraction region. Additionally, there may be a seal member located between the first blood component extraction tube and the bottom core to prevent leakage between the first blood component extraction tube and the bottom core.

In some embodiments, the bowl may include an optical sensor located on a shoulder of the outer body. The optical sensor may monitor an interface between the first blood component and the second blood component within the separation region, and control the operation of a first blood component pump based upon a location of the interface. The first blood component pump may draw the first blood component from the centrifuge bowl.

Additionally, the bowl may have a weir disk extending inward from the neck portion of the outer body. The second blood component may flow over the weir disk into the neck portion of the outer body prior to exiting the centrifuge bowl via the second blood component outlet port. The weir disk and a top surface of the top core can define a second blood component channel that fluidly connects the separation region and the second blood component outlet port.

The centrifuge bowl may also have a bottom core with a bottom wall and a proximally extending wall that extends from the bottom core. The proximally extending wall may be radially outward from at least a portion of the top core. The proximally extending wall and a portion of the top core may define a primary separation region that is fluidly connected to the secondary separation region. The bowl may also have a fluid path that extends between a bottom wall of the top core and an upper surface of the bottom core, and fluidly connects the inlet tube and the primary separation region. A first blood component extraction region (located between the bottom wall of the bottom core and a bottom of the outer body) may fluidly connect the first blood component extraction tube and the separation region. The proximally extending wall may prevent whole blood from entering the first blood component extraction region. The introduction region may be located between the top core and the bottom core.

In accordance with still further embodiments, a centrifuge bowl for continuous separation of whole blood may include an outer body, a top core, and a separation region. The outer body may be rotatable about a longitudinal axis of the centrifuge bowl, and may have a main body defining an interior cavity, a neck portion extending proximal to the main body, and a shoulder connecting the main body and the neck portion. The top core may be located within and rotatable with the outer body. The top core may also be coaxial with the outer body and include a chimney extending through it along the longitudinal axis of the centrifuge bowl. The separation region may be located between the top core and the outer body, and rotation of the centrifuge bowl may separate the whole blood within the separation region into a first blood component and a second blood component.

The bowl may also include an inlet port, a first blood component outlet port, and a second blood component outlet port. The inlet port may introduce whole blood into the centrifuge bowl, and may be fluidly connected to an inlet tube that extends distally from the inlet port and through the chimney to introduce the whole blood into an introduction region. The first blood component outlet port may draw a first blood component out of the centrifuge bowl, and may have a first blood component extraction tube that extends from the first blood component outlet port to a first blood component extraction region. The second blood component outlet port may be fluidly connected to the separation region and may be configured to draw a second blood component from the centrifuge bowl. The bowl may also have a rotary seal that is attached to the outer body and fluidly couples the inlet port, first blood component outlet port, and second blood component outlet port to the outer body.

Additionally, the bowl may also have a weir disk extending inward from the neck portion of the outer body. In such embodiments, the second blood component may flow over the weir disk and into the neck portion of the outer body prior to exiting the centrifuge bowl via the second blood component outlet port. The weir disk and the top surface of the top core may define a second blood component channel that fluidly connects the separation region and the second blood component outlet port.

Located between the bottom surface of the outer body and the top core, the bowl may also have a bottom core that is rotatable with the outer body. The first blood component extraction region may be located between the bottom wall of the bottom core and a bottom of the outer body, and may fluidly connect the first blood component outlet tube and the separation region. The first blood component extraction tube may extend through the bottom core and into the first blood component extraction region, and a seal member located between the first blood component extraction tube and the bottom core may prevent leakage between the first blood component extraction tube and the bottom core.

The bottom core may have a bottom wall and a proximally extending wall that is radially outward from at least a portion of the top core. The proximally extending wall and at least a portion of the top core may define a primary separation region that is fluidly connected to the secondary separation region. The bowl may also have a fluid pathway fluidly connecting the inlet tube and the primary separation region. The fluid pathway may extend between a bottom wall of the top core and an upper surface of the bottom core. The proximally extending wall may prevent whole blood from entering the first blood component extraction region.

The outer body may include an optical sensor that (1) monitors an interface between the first blood component and the second blood component within the separation region, and (2) controls the operation of a first blood component pump based upon a location of the interface. The first blood component pump may draw the first blood component from the centrifuge bowl. The inlet tube and the first blood component extraction tube may extend through the chimney and may be coaxial. The bowl may also include a bypass seal (e.g., a rotary seal) between an outer diameter of the inlet tube and an inner diameter of the chimney that isolates the introduction region from the chimney.

In accordance with additional embodiments, a centrifuge bowl for continuous separation of whole blood may include an outer body rotatable about a longitudinal axis of the bowl, a top core located within and rotatable with the outer body, and a separation region located between the top core and the outer body. The outer body may have a main body defining an interior cavity, a neck portion extending proximal to the main body, and a shoulder connecting the main body and the neck portion. The top core may be coaxial with the outer body and may include a chimney extending through it along the longitudinal axis of the centrifuge bowl. Rotation of the centrifuge bowl may separate the whole blood within the separation region into a first blood component and a second blood component.

The bowl may also have a rotary seal attached to the outer body and fluidly coupling an inlet port, a first blood component outlet port, and a second blood component outlet port to the outer body. The inlet port may be used to introduce whole blood into the centrifuge bowl, and may be fluidly connected to an inlet tube. The inlet tube may extend distally from the inlet port and through the chimney to introduce the whole blood into an introduction region. The first blood component outlet port may be used to draw the first blood component out of the centrifuge bowl, and may include a first blood component extraction tube extending from the first blood component outlet port to a first blood component extraction region. The second blood component outlet port may be fluidly connected to the separation region and may be used to draw a second blood component from the centrifuge bowl.

Moreover, the bowl may also have an optical sensor located on the shoulder of the outer body. The optical sensor may monitor an interface between the first blood component and the second blood component within the separation region, and control the operation of a first blood component pump based upon a location of the interface. The first blood component pump may draw the first blood component from the centrifuge bowl.

A bottom core located below the top core can have a bottom wall and a proximally extending wall. The first blood component extraction region may be located between the bottom wall of the bottom core and a bottom of the outer body, and may fluidly connect the first blood component outlet tube and the separation region. The first blood component extraction tube may extend through the bottom wall of the bottom core, and the bowl may include a seal member located between the first blood component extraction tube and the bottom wall of the bottom core. The seal member may prevent leakage between the first blood component extraction tube and the bottom core.

The proximally extending wall may be radially outward from at least a portion of the top core, and may define a primary separation region with at least a portion of the top core. The primary separation region may be fluidly connected to the secondary separation region, and the bowl may include a fluid pathway (e.g., extending between a bottom wall of the top core and an upper surface of the bottom core) that fluidly connects the inlet tube and the primary separation region. The separation chamber may be in fluid communication with the second blood component outlet.

The first blood component extraction tube and the inlet tube may be coaxial and may extend through the chimney. The bowl may include a bypass seal (e.g., a rotary seal) between an outer diameter of the inlet tube and an inner diameter of the chimney that isolates the introduction region from the chimney. Additionally, a weir disk extending inward from the neck portion of the outer body may define a second blood component channel with a top surface of the top core. The second blood component channel may fluidly connect the secondary separation region and the second blood component outlet port. The second blood component may flow over the weir disk into the neck portion of the outer body prior to exiting the centrifuge bowl via the second blood component outlet port.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, a continuous flow separation chamber is able to process and separate whole blood into its various components, and allows for the extraction of multiple blood components (e.g., red blood cells, plasma, etc.) simultaneously and while the separation chamber is spinning. In this manner, various embodiments of the present invention are able to continuously process whole blood and avoid the drawbacks of the batch/intermittent processes described above.

Figure 1:
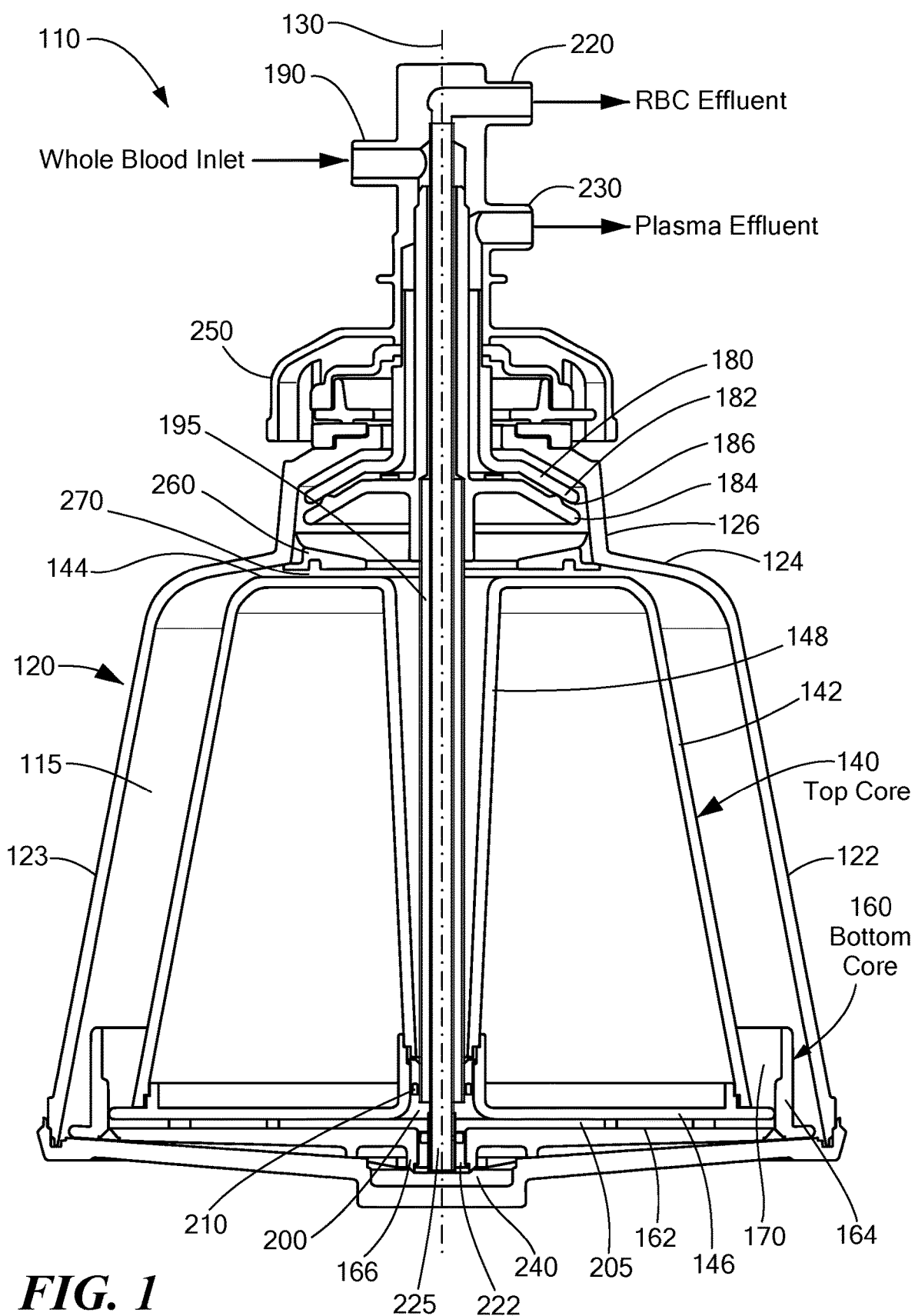
FIG. 1 schematically shows a cross-sectional view of a continuous flow centrifuge bowl in accordance with illustrative embodiments of the present invention.

FIG. 1 schematically shows a cross-section of a continuous flow separation chamber (e.g., a centrifuge bowl 110), in accordance with some embodiments of the present invention. The bowl 110 has an outer body 120 that defines the structure of the bowl 110 and an inner volume into which the whole blood may be introduced for processing. The outer body 120, in turn, includes a main wall 122 that defines a main body portion 123, a neck portion 126, and shoulder portion 124 that connects the main body portion 123 and the neck portion 126. As discussed in greater detail below, the bowl 110 is rotatable about an axis 130 in order to separate the whole blood into its various components.

Within the interior of the outer body 120, the bowl can include a number of cores that displace some of the volume within the outer body 120, create separation regions in which the whole blood separates, and create a number of fluid paths/channels within the bowl 110. For example, the bowl 110 may include a top core 140 that fills a significant portion of the inner volume and may be frusto-conical in shape. The top core 140 includes a top surface 144, a bottom wall 146, and a side wall 142 that extends between the top surface 144 and the bottom wall 146. The side wall 142 may be spaced from the main wall 122 (e.g, the main body 123) to create a separation region (e.g., a secondary separation region 115) between the side wall 142 of the top core 140 and the main wall 122 of the outer body 120. Additionally, the top core 140 can have a chimney 148 extending through the center from the top surface 144 to the bottom wall 146. As discussed in greater detail the chimney 148 may serve as a channel through which a number of tubes (e.g., an inlet tube and an extraction tube) can pass.

Figure 2:
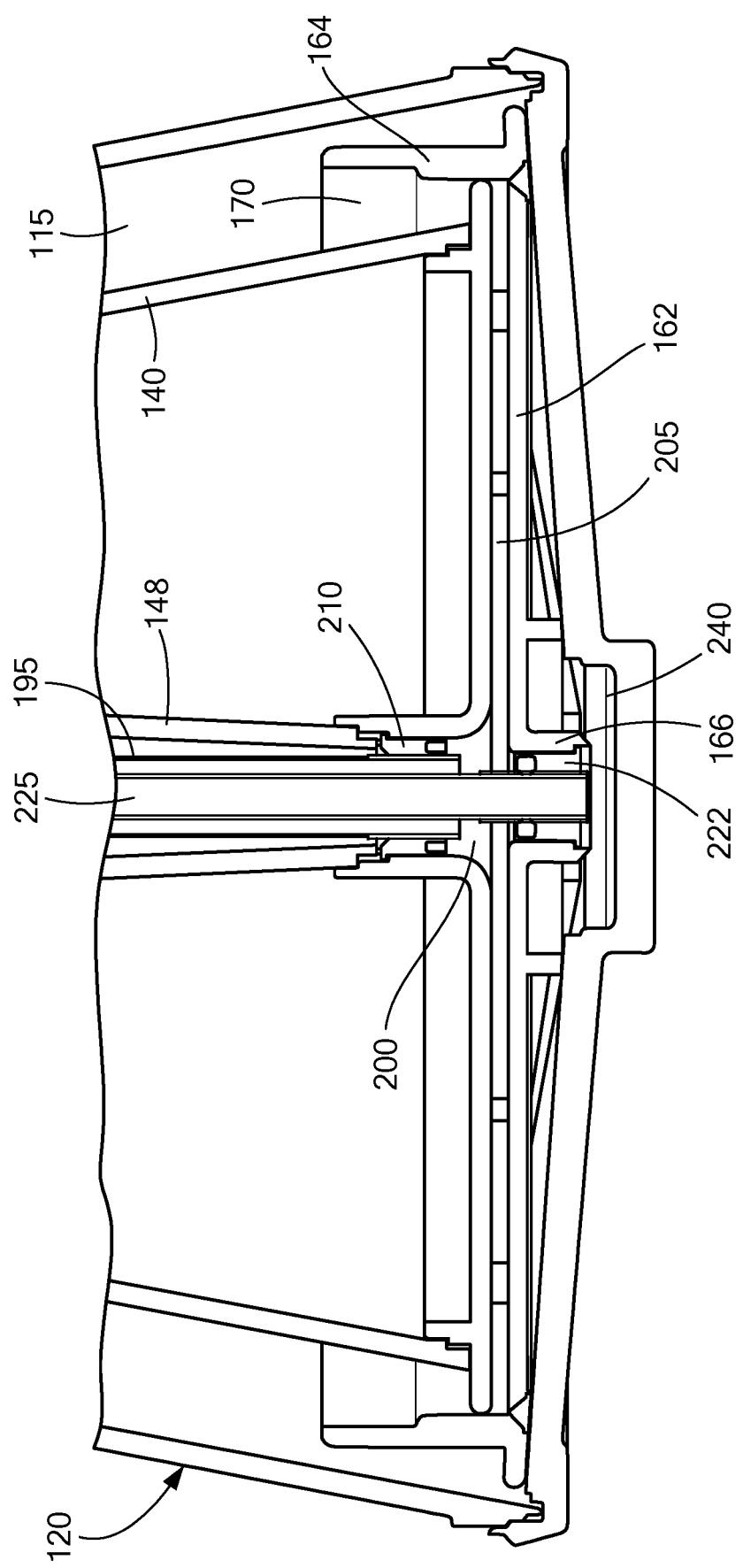
FIG. 2 schematically shows a cross-sectional view of the lower portion of the centrifuge bowl shown in FIG. 1 with an alternative bottom core, in accordance with illustrative embodiments of the present invention.

The bowl 110 may also include a bottom core 160 (FIG. 2) located below the top core 130 (e.g., distal to the top core 130). The bottom core 160 may include a bottom circular wall 162 with an opening 166 extending through it (e.g., near the center of the circular wall 162). The bottom core 160 may also have a vertical wall 164 that extends upward (e.g., proximally) from the bottom circular wall 162. As shown in FIGS. 1 and 2, the vertical wall 164 is located near the outer diameter of the bottom circular wall 162 and may extend upwards such that it is radially outward from the side wall 142 of the top core 140. The annular space between the side wall 142 of the top core 140 and the vertical wall 164 creates a primary separation region 170 in which separation of whole blood begins (discussed in greater detail below). Although similar, it is important to note that the bottom core 160 shown in FIG. 2 is an alternative embodiment of the bottom core 160 shown in FIG. 1 (e.g., it is thinner than that shown in FIG. 1).

Figure 4:
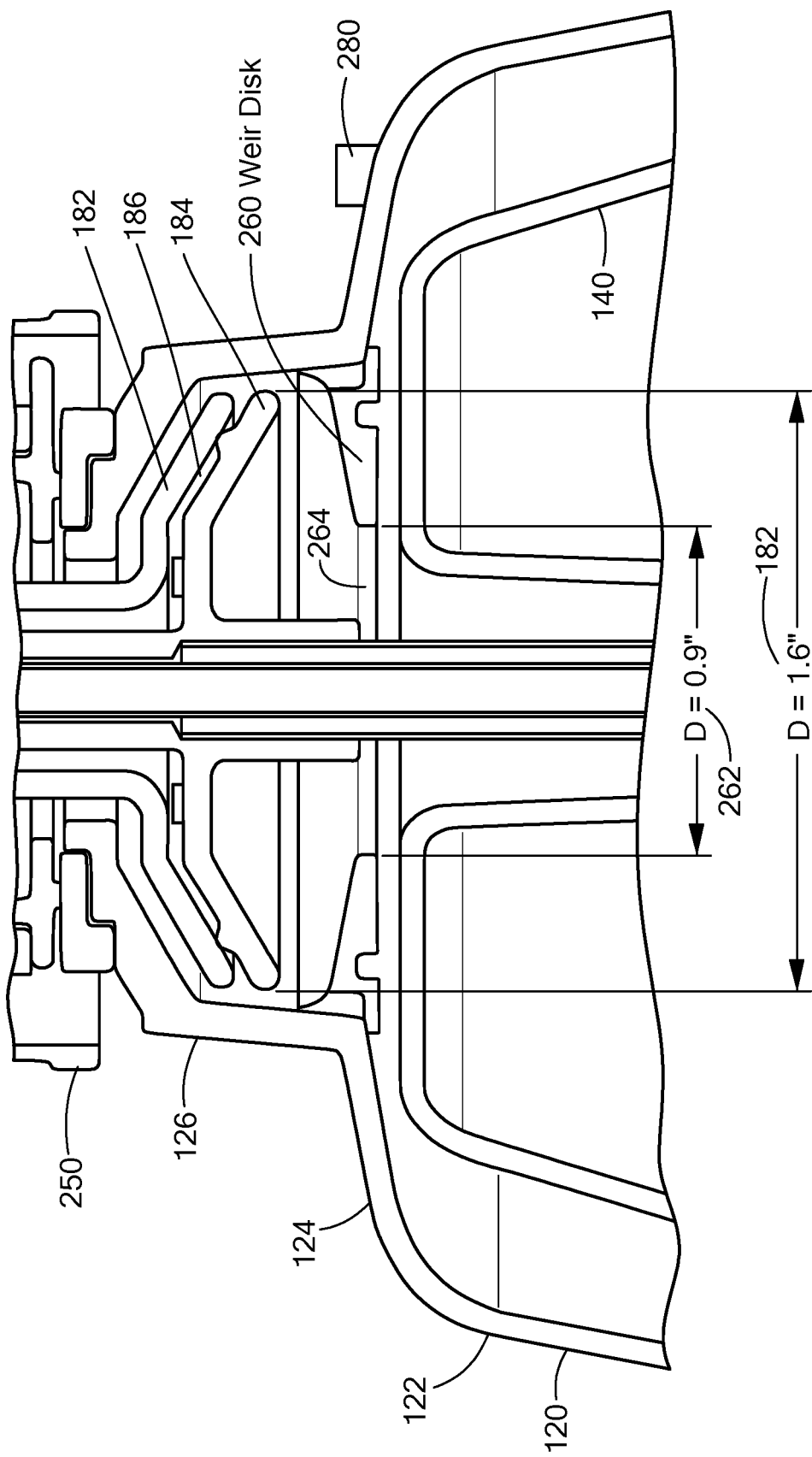
FIG. 4 schematically shows a cross-sectional view of the top portion of the centrifuge bowl shown in FIG. 1, in accordance with illustrative embodiments of the present invention.

As best shown within FIG. 4, within the neck portion 126 of the outer body 120, the centrifuge bowl 110 can include a upper skirt 182 and a lower skirt 184 both extending radially outward from the center of the bowl 110. Together, the upper skirt 182 and the lower skirt 184 can form an effluent skirt 180 through which one or more of the separated blood components can flow and exit the bowl 110 (e.g., via the second blood component outlet 230, discussed in greater detail below). To that end, the upper skirt 182 and the lower skirt 184 may be spaced from one another such that an effluent channel 186 is formed between the skirts 182/184. The exiting blood component can flow through the effluent channel 186 to reach the second blood component outlet 230.

In order to facilitate the transfer of fluids (e.g., whole blood and blood components) in and out of the centrifuge bowl 110, the bowl 110 can have an inlet and one or more outlets. For example, the bowl 110 may include an inlet 190 that may be used to introduce whole blood into the bowl 110. In many blood processing procedures, it is desirable to introduce the whole blood into an area near the bottom of the bowl 110. To that end, some embodiments of the present invention may also include an inlet tube 195 that extends downward from the inlet 190, through the chimney 148 in the top core 140, and into an introduction region 200 located between the top core 140 and the bottom core 160. Additionally, the bottom core 160 (e.g., the circular wall 162) may be spaced from the bottom 146 of the top core 140 to create a channel 205 extending from the introduction region 200 to the primary separation region 170. The centrifugal force created by spinning the bowl 110 may cause the whole blood entering the introduction region 200 to flow through the channel 205 and into the primary separation region 170.

Figure 3:
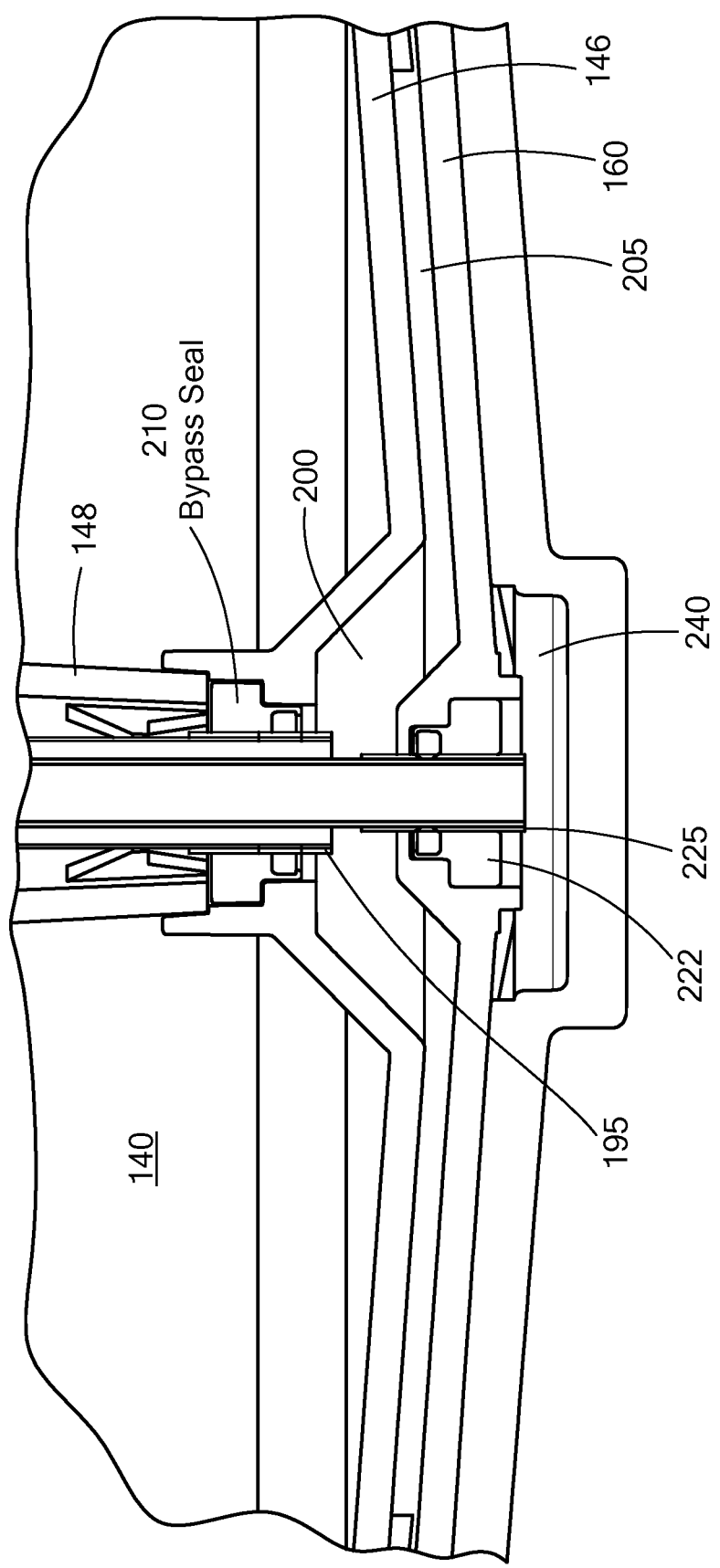
FIG. 3 schematically shows a cross-sectional view of a bypass seal within the centrifuge bowl shown in FIG. 1, in accordance with illustrative embodiments of the present invention.

It is important to note that problems can arise if the whole blood or other fluid introduced into the bowl 110 (e.g., into the introduction region 200) flows back up into the chimney 148 (e.g., instead of traveling towards the outer diameter of the bowl 110 and into the separation regions). For example, if this "bypass" occurs while the bowl 110 is being filled, unseparated red blood cells may flow up the chimney 148, and contaminate the effluent plasma exiting the bowl 110. If the bypass occurs during a surge step (e.g., to remove platelets from the bowl 110, discussed in greater detail below), plasma may travel up the chimney 148 instead of carrying away the platelets. In order to avoid this "bypass" and isolate the introduction region 200 from the chimney 148 in the top core 130, some embodiments of the present invention can include a bypass seal 210 (FIG. 3) located between the outer diameter of the inlet tube 195 and the inner diameter of the chimney 148. The bypass seal 210 can be a rotary seal to allow the top core 130 (and the bowl 110) to rotate relative to the inlet tube 195 (which does not rotate during bowl operation).

In addition to the inlet 190, the bowl 110 can also include a first blood component outlet 220 and a second blood component outlet 230. As the name suggests, the first blood component outlet 220 can be used to remove a first blood component (e.g., red blood cells) from the bowl 110. Additionally, in a manner similar to the inlet 190, the first blood component outlet 220 may be fluidly connected to a tube (e.g., a first blood component extraction tube 225) that extends downward from the first blood component outlet 220, through the chimney 148, through the opening 166 in the bottom core 160 (e.g., within the bottom circular wall 162), and into a first blood component extraction region 240 located below the bottom bore 160 (e.g., between the bottom core 160 and the bottom of the bowl 110). To prevent leakage past the bottom core 160 (e.g., through opening 166), the bowl 110 can also have a seal 222 (e.g., a rotary seal) between the first blood component extraction tube 225 and the opening 166. As discussed in greater detail below, a pump can draw the first blood component out of the first blood component extraction region 240, through the first blood component extraction tube 225 and out of the first blood component outlet 220.

The second blood component outlet 230 may be used to remove the second blood component (and perhaps a third) from the bowl 110. To that end, the second blood component outlet 230 may be fluidly connected to the effluent channel 186 through the effluent skirt 180. Therefore, when the second blood component is pushed towards the neck portion 126 (e.g., as discussed in greater detail below), the second blood component can flow through the effluent channel 186 and out of the second blood component outlet 230.

As best shown in FIGS. 1 and 4, the centrifuge bowl 110 may include a rotary seal 250 that connects the ports (e.g., the inlet 190, first blood component outlet port 220, and second blood component outlet port 230) to the outer body 120 of the bowl 110. The rotary seal 250 allows the bowl 110 (and the top core 140 and bottom core 160) to spin while the the inlet 190, first blood component outlet 220, and second blood component outlet 230 remain stationary.

It is important to note that in some applications, in order to extract the first blood component (e.g., red blood cells) from the bowl 110 (e.g., from the first blood component extraction region 240), a large negative pressure may be required to overcome the centrifugal force created as the bowl 110 spins. For example, it was discovered that the radius of the air cylinder defined by the diameter 182 of the effluent skirt 180 (e.g., a cylinder of air below the effluent skirt 180) drives the negative force required to draw out the first blood component. In some applications, the pressures required to draw out the first blood component can be greater than 500 mmHG ($P = \rho g r$, where $\rho$ is the density of the fluid, g is the centrifugal force and r is the radius of the air cylinder), which is impractical for any type of available pumping technology.

In order to reduce the pressure required to withdraw the first blood component, some embodiments of the present invention can include a weir disk 260 (FIG. 4) that extends radially inward from the bottom of the neck portion 126 of the outer body 120. The weir disk 260 essentially creates a wall that forces fluid leaving the bowl 110 to a smaller diameter defined by the inner diameter 262 of the opening 264 through the weir disk 260. In this manner, the weir disk 260 essentially decouples the diameter of the effluent skirt 180 from the radius of the air cylinder, which, in turn, reduces the radius of the air cylinder (which is now defined by diameter 262 of the opening 264 in the weir disk 260) and the pressure required to withdraw the first blood component from the bowl 110.

As shown in FIG. 4, the weir disk 260 creates a fluid channel 270 between the weir disk 260 and the top surface 144 of the top core 140. As the bowl 110 fills with fluid, the fluid will flow through the fluid channel 270 between the weir disk 260 and the top surface 144 of the top core 140 until it reaches the opening 264 in the weir disk 260. The fluid may then "roll over" the weir disk 260 (e.g., similar to the overflow of a dam), and fill the region above the weir disk 260 (e.g., the neck portion 126 of the bowl 110) until it comes in contact with the effluent skirt 180. The fluid (e.g., the second blood component) may then be pushed from the bowl 110 into the effluent channel 186 and into the second blood component outlet 230.

During blood processing it is important to know not only how full the bowl 110 is but also the location of the red blood cell/plasma interface within the secondary separation chamber 115. To that end, some embodiments may include an optical system 280 located on the shoulder 124 of the outer body 120. The optical system 280 may include an LED (e.g., a red LED) that emits a beam (e.g., approximately 1-2 mm in diameter) that illuminates a small area of the shoulder 124. Additionally, the optical system 280 may also include an optical sensor that is focused on the illuminated area of the bowl shoulder 280.

As the plasma/cell interface encroaches on this illuminated area, the signal received back at the sensor decreases. The optical system 180 may be in communication with a control system of the blood processing device, and when the optical system 280 identifies that this signal has decreased by some predetermined amount (e.g. 10%), the control system may increase the speed of a pump (e.g., a red blood cell pump, discussed in greater detail below) that is drawing the first blood component out of the bowl by some predetermined amount (e.g. 5 ml/min). If the reading from the optical sensor continues to decrease, the control system may continue to increase the speed of the pump. When the output from the optical sensor begins to plateau and no longer change, the control system will maintain the speed of the pump. Conversely, if the output signal begins to increase, the control system will slow down the pump, pushing the interface further in towards the area of illumination. In this manner, various embodiments of the invention are able to monitor and control the location of the plasma/cell interface to ensure that the interface remains in the optimal location within the bowl 110.

Figure 5:
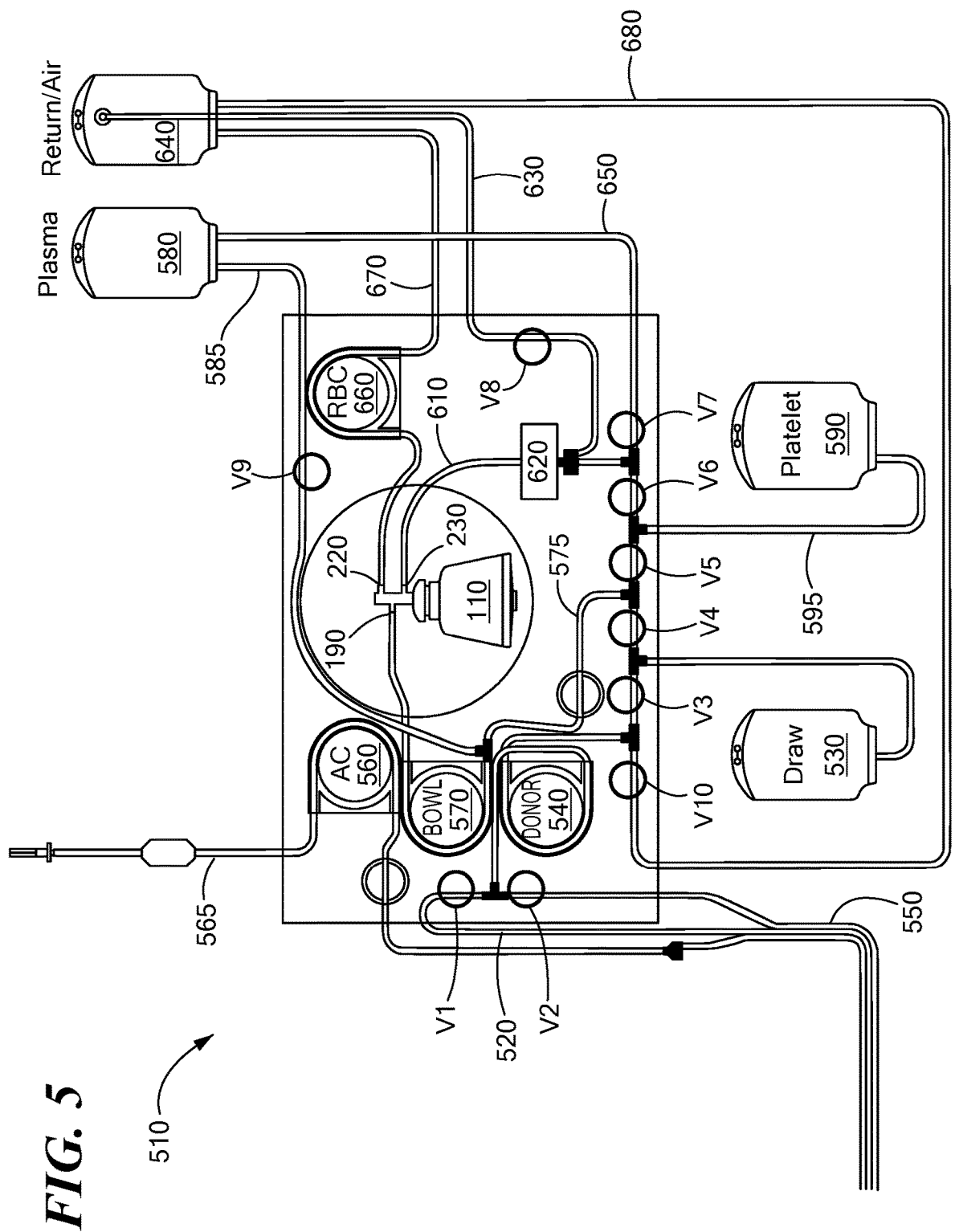
FIG. 5 is a schematic diagram of a continuous flow blood processing system using the centrifuge bowl shown in FIG. 1, in accordance with illustrative embodiments of the present invention.

FIG. 5 schematically shows an exemplary blood processing system 510 utilizing the centrifuge bowl 110 described above and shown in FIG. 1. FIG. 5 will be discussed in conjunction with an exemplary blood processing method. First, whole blood may be drawn from source (e.g., a patient, a blood storage bag, etc.), through a draw line 520, and into a storage container (e.g., draw bag 530) using a donor pump 540. During this draw step, the donor pump 540 may run in a clockwise direction and valves V1 and V3 may be open to allow the whole blood to flow into the draw bag 530, and valves V2 and V4 may be closed to prevent the whole blood from entering a return line 550. Also, while the whole blood is being drawn from the source, an anticoagulant pump 560 may draw anticoagulant through an anticoagulant line 565 from an anticoagulant source (not shown). The anticoagulant may mix with the drawn whole blood prior to reaching the draw bag 530. In some embodiments, the draw pump 540 may draw approximately 75-80 mL of whole blood at approximately 120 mL/min during this initial draw phase.

Once the initial draw step has commenced and a sufficient amount of anticoagulated whole blood is collected in the draw bag 530, a bowl pump 570 may begin to draw anticoagulated whole blood from the draw bag 530 via line 575. As the bowl pump 570 draws the anticoagulated whole blood from the bag 530, valve V4 may be opened to allow the anticoagulated whole blood to flow into line 575, and valves V5 and V9 may be closed to prevent the anticoagulated whole blood from flowing into the plasma bag 580 via the plasma recirculation line 585 and/or the platelet bag 590 via the platelet line 595. In order to ensure that a sufficient volume of anticoagulated whole blood remains within the draw bag 530 (e.g., to maintain a continuous flow of anticoagulated whole blood to the bowl 110), the bowl pump 570 may draw the anticoagulated whole blood from the bag at a rate slower than that of the donor pump 540. For example, the bowl pump 570 may draw at a rate of 60 mL/min as compared to the donor pump's rate of 120 mL/min. The bowl 110 will continue to fill until the optical system 280 detects the presence of the plasma/cell interface.

As the anticoagulated whole blood enters the bowl 110 through the inlet 190, it will flow down the inlet tube 195 and into the introduction region 200. Once in the introduction region 200, the centrifugal forces from the spinning of the bowl 110 will cause the anticoagulated whole blood to flow through the channel 205 between the top core 140 and bottom core 160 and into the primary separation region 170 (e.g., between the side wall 142 of the top core 140 and the proximally extending wall 164 of the bottom core), where separation of the anticoagulated whole blood into its individual components (e.g., plasma, platelets, red blood cells) begins.

As additional anticoagulated whole blood is introduced into the bowl 110, the whole blood will flow into the secondary separation region 115 where the anticoagulated whole blood continues to separate. For example, as the whole blood enters the secondary separation region 115 of the bowl 110, the centrifugal forces cause the heavier cellular components of the blood to sediment from the lighter plasma component of the blood. This results in the cell/plasma interface mentioned above. The red blood cells are by far the most numerous of the cellular components of blood and the most dense, resulting in a layer of concentrated red blood cells at the outermost diameter of the bowl 110. As filling continues, the other cellular components of blood begin to become apparent. These cellular components are primarily platelets, leukocytes and peripheral hematopoietic progenitor stem cells. These cells may have a range of densities between that of the red blood cells and plasma. Therefore they tend to sediment in a layer between the red blood cell layer and plasma layer. As this layer grows, it is visually apparent as a solid white layer which is known as a buffy coat.

As the bowl 110 continues to fill with whole blood, the red blood cells will continue to sediment to the outermost diameter, flow over the proximally extending wall 164 on the bottom core 160, and begin to fill the area between the bottom core 160 and the bottom of the bowl 110. Additionally, the intermediate cells of the buffy coat will continue to accumulate at the red blood cell/plasma interface, and the plasma interface will move inward towards the center of the bowl 110. When the bowl 110 is full, the plasma will flow through the fluid channel 270 between the weir disk 260 and the top surface 144 of the top core 140, over the weir disk 260, and will exit the bowl 110 via the effluent channel 186 and the second blood component outlet 230.

As the plasma exits the bowl 110, the majority of the plasma may pass through line 610, valve V8, line 630 and into a return bag 640. However, a small volume of plasma (e.g., 175-200 mL over the length of the procedure) may be sequestered within the plasma bag 580. To sequester this plasma in the plasma bag 580, the operator or the control system can open valve V7 to allow some of the plasma exiting the bowl 110 to enter line 650 and flow into the plasma bag 580. As discussed in greater detail below, the sequestered plasma in the plasma bag 580 will be used during a surge elutriation procedure to remove the platelets from the bowl 110.

As mentioned above, the bowl 110 is a continuous flow bowl that allows the continuous processing of whole blood without the need to intermittently stop. To that end, various embodiments of the present invention also extract red blood cells from the bowl 110 as additional whole blood is introduced (e.g., while simultaneously extracting plasma). For example, once the red blood cells have collected under the bottom core 160 (e.g., in the first blood component extraction region 240), the red blood cell pump 660 can draw red blood cells inward of the air cylinder diameter (e.g., corresponding to the diameter of the effluent skirt 180 or the opening 264 through the weir disk 180, if equipped), into the first blood component extraction region 240, up the first blood component extraction tube 225 and out of the first blood component outlet 220. As the red blood cells leave the bowl 110, they will pass through line 670 and into the return bag 640. While the red blood cell pump 660 extracts the red blood cells, the optical system 280 will monitor the location of the plasma/cell interface and will control the flow rate of the red blood cell pump 660 to adjust the location of the interface as necessary (e.g., it will speed up the pump 660 if the sensor output decrease and slow down the pump 660 if the sensor output increases).

Once the donor pump 540 has drawn a predetermined volume of whole blood from the source (e.g., 80 mL), the system 510 will stop the draw step and begin to return some of the blood components (e.g., red blood cells and plasma) that have been collected in the return bag 640. For example, the system 510 will reverse the direction of the donor pump 540, close valves V1 and V3, and open valves V2 and V10. This will cause the donor pump 540 to begin drawing (e.g., at 120 mL/min) the plasma and red blood cells within the return bag 640 through line 680, valves V10 and V2, through a return line 550 and back to the source (e.g., back to the patient). This return phase will continue until a predetermine volume of red blood cells and plasma are returned to the subject, for example, 80 mL. The system 510 may then alternate the draw and return phases until the procedure is complete.

It is important to note that, because this is a continuous system, anticoagulated whole blood is continuously drawn from the draw bag 530 and into the bowl 110, even during the return phase. As mentioned above, this can be accomplished by first drawing a bolus volume of whole blood from the subject, collecting the bolus volume of whole blood within the draw bag 530, and drawing the whole blood from the draw bag at a slower rate than the draw and return steps (e.g., the bowl pump 570 draws the anticoagulated whole blood at 60 mL/min and the donor pump 540 draws the whole blood from the subject and returns the red blood cells and plasma to the subject at 120 mL/min). Therefore, the draw bag always has a sufficient volume of anticoagulated whole blood from which the bowl pump 570 can draw.

The whole blood processing may continue until a desired volume of platelets has accumulated within the bowl 110. When the blood processing is complete, the system 510 may then perform a surge elutriation process using the sequestered plasma in order to extract the highly concentrated platelet product. For example, the bowl pump 570 can draw the plasma within the plasma bag 580, through plasma recirculation line 585 and valve V9, and into the bowl 110 (e.g., via the inlet 190). To elutriate the platelets, the flow rate of plasma is gradually increased. As the flow rate is increased, the effluent plasma passes through a line sensor 620 (located on line 610) that monitors the fluid exiting the bowl 110. At some point in this ramping up of plasma flow rate, the drag force created by the plasma flow overcomes the centrifugal force caused by the bowl rotation, and the platelets are carried away from the buffy coat in the flowing plasma. The line sensor 620 may then detect the presence of cells (e.g., as the fluid exiting the bowl 110 changes from plasma to platelets), and the system 510 (or the user) can close valve V7 and open valve V6 to allow the platelets to flow into the platelet line 595 and into the platelet bag 590.

After the elutriation process and after the platelets are collected within the platelet bag 590, the system 510 may stop the bowl 110 and return the contents of the bowl 110 to the donor For example, the system 510 may turn on the red blood cell pump 660 to draw the contents of the bowl 110 into the return bag 640 (via line 670). The donor pump 540 may then draw the contents of the return bag 640 through line 680, and return the components via the return line 550.

It should be noted that, although the blood processing method discussed above draws whole blood from and returns the contents of the bowl to a donor, some embodiments may not draw from and/or return to a donor. Rather, in some embodiments, the whole blood may be drawn from a whole blood storage container, and the contents of the bowl 110 may be returned to the whole blood storage container (or a different blood storage container).

Figure 6:
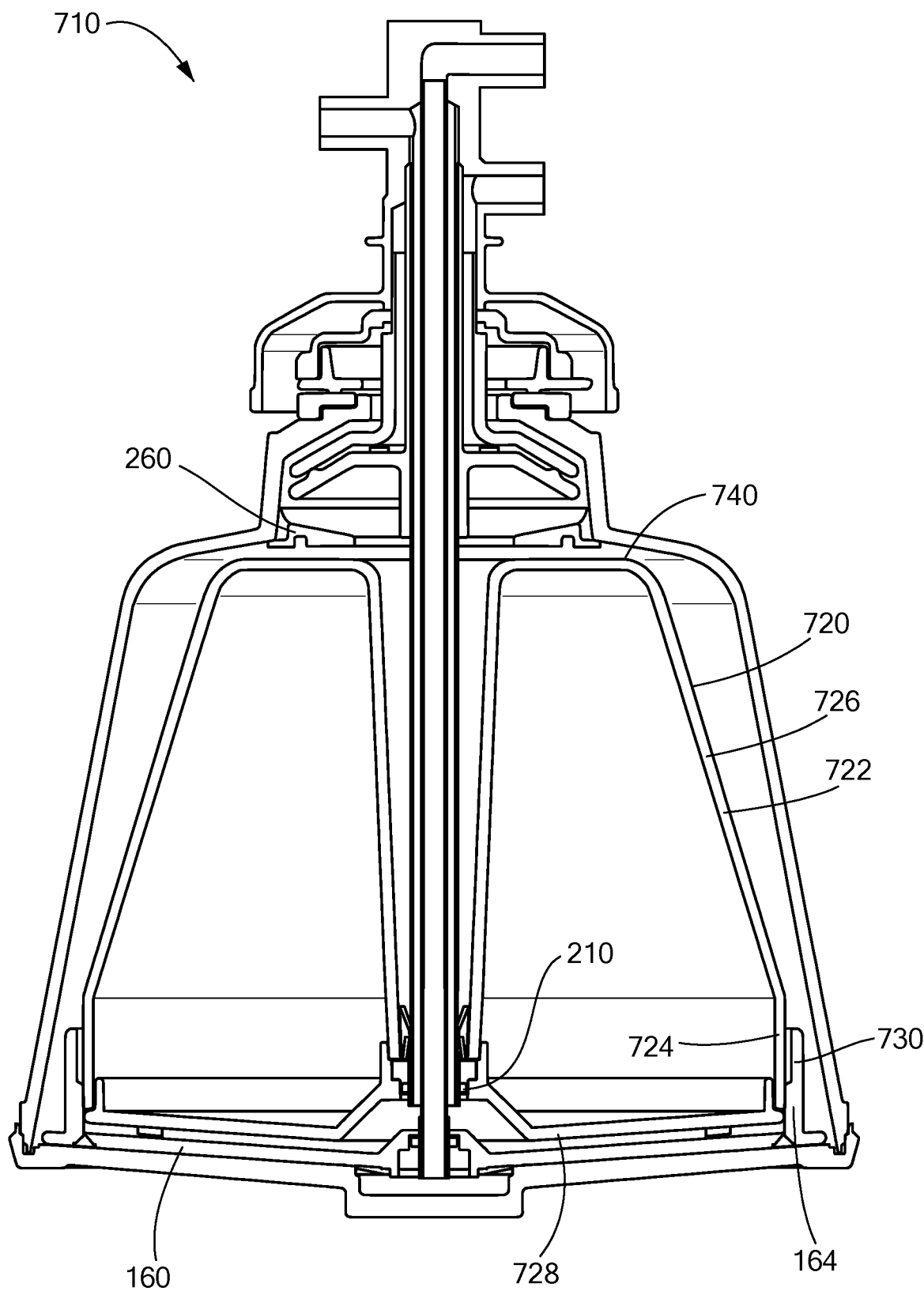
FIG. 6 schematically shows a cross-sectional view of an alternative continuous flow centrifuge bowl in accordance with illustrative embodiments of the present invention.
Figure 7:
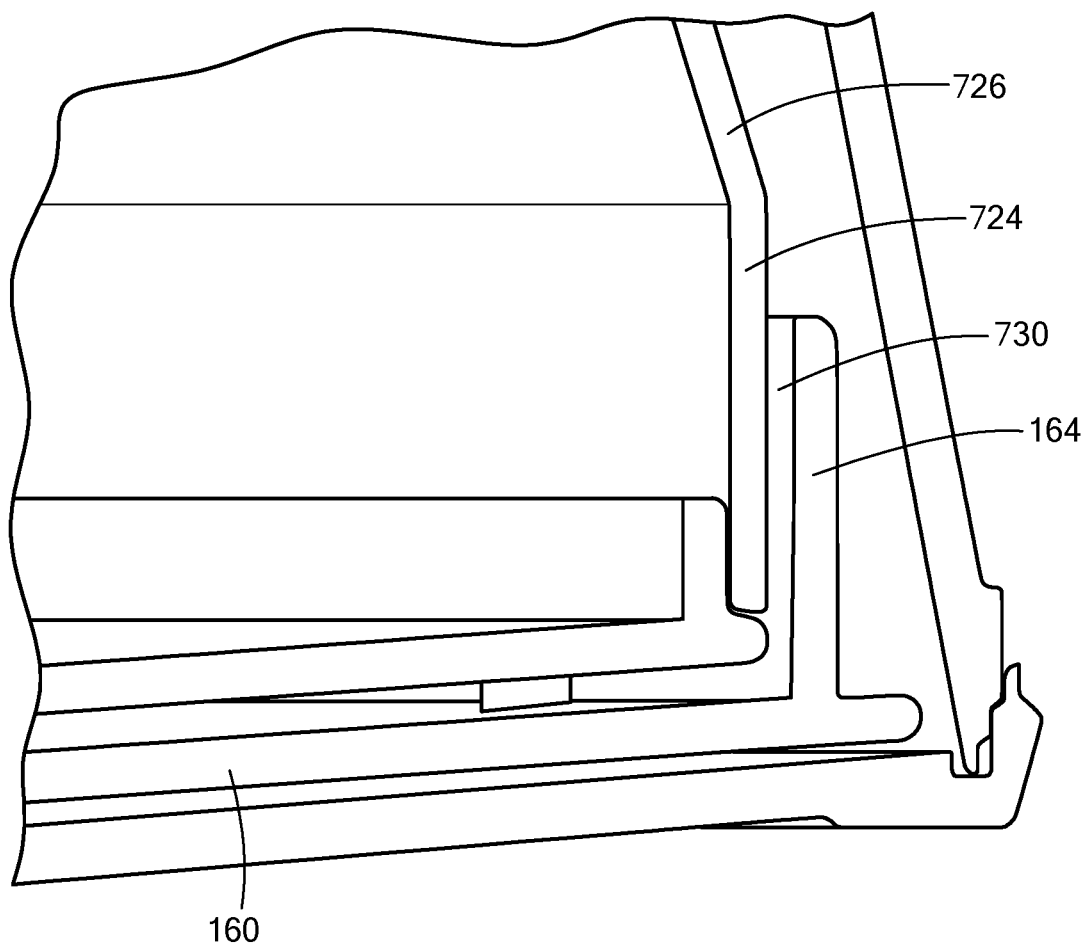
FIG. 7 schematically shows a cross-sectional view of the lower portion of the centrifuge bowl shown in FIG. 6, in accordance with illustrative embodiments of the present invention.

It is also important to note that although the centrifuge bowl 110 discussed above and shown in FIG. 1 has a sloped wall 142 on the top core 140 (e.g., it is angled such that the diameter of the top core 140 increases from the top surface 144 to the bottom 146), other embodiments can have different configurations. For example, as shown in FIGS. 6 and 7, some embodiments of the bowl 710 can have a top core 720 with a side wall 722 having a straight section 724 and an angled/sloped section 726. The straight walled section 724 can extend a distance from the bottom 728 of the top core 720 and may be located radially inward from the proximal wall 164 of the bottom core 160. The primary separation region 730 may be located between (and defined by) the straight walled section 724 of the top core 720 and the proximally extending wall 164 of the bottom core 160. The angled/sloped wall/section 726 can extend from the top of the straight walled portion 724 to the top surface 740 of the top core 720.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A centrifuge bowl for continuous separation of whole blood comprising:
    an outer body rotatable about a longitudinal axis of the centrifuge bowl, the outer body having a main body defining an interior cavity, a neck portion extending proximal to the main body, and a shoulder connecting the main body and the neck portion;
    a top core located within and rotatable with the outer body, the top core being coaxial with the outer body and including a chimney extending through the top core along the longitudinal axis of the centrifuge bowl;
    a separation region located between the top core and the outer body, rotation of the centrifuge bowl separating the whole blood within the separation region into a first blood component and a second blood component;
    an inlet port for introducing whole blood into the centrifuge bowl;
    an inlet tube fluidly connected to and extending distally from the inlet port and through the chimney, the inlet tube configured to introduce the whole blood into an introduction region;
    a first blood component outlet port for drawing the first blood component out of the centrifuge bowl;
    a first blood component extraction tube extending from the first blood component outlet port to a first blood component extraction region located below a bottom core, the first blood component extraction tube coaxial with and extending at least partially through the inlet tube;
    a seal member located between the first blood component extraction tube and the bottom core, the seal member preventing leakage between the first blood component extraction tube and the bottom core;
    a second blood component outlet port fluidly connected to the separation region and for drawing a second blood component from the centrifuge bowl;
    a centrifuge bowl rotary seal attached to the outer body and fluidly coupling the inlet port, first blood component outlet port, and second blood component outlet port to the outer body; and
    an optical sensor located on the shoulder of the outer body, the optical sensor configured to monitor an interface between the first blood component and the second blood component within the separation region, the optical sensor configured to control the operation of a first blood component pump based upon a location of the interface.

2. A centrifuge bowl according to claim 1 wherein the first blood component pump is configured to draw first blood component from the centrifuge bowl.

3. A centrifuge bowl according to claim 1, further comprising the bottom core, the bottom core having a bottom wall and a vertically extending wall, the first blood component extraction region located between the bottom wall of the bottom core and a bottom of the outer body, the first blood component extraction region fluidly connecting the first blood component outlet tube and the separation region.

4. A centrifuge bowl according to claim 3, wherein the first blood component extraction tube extends through the bottom wall of the bottom core and into the first blood component extraction region.

5. A centrifuge bowl according to claim 4, wherein the seal member is located between the first blood component extraction tube and the bottom wall of the bottom core.

6. A centrifuge bowl according to claim 1, wherein the separation region is in fluid communication with the second blood component outlet port.

7. A centrifuge bowl according to claim 1, wherein the first blood component is red blood cells and the second blood component is plasma.

8. A centrifuge bowl according to claim 1, further comprising the bottom core, the bottom core having a bottom wall and a vertically extending wall extending from the bottom core, the vertically extending wall being radially outward from at least a portion of the top core.

9. A centrifuge bowl according to claim 8, further comprising a primary separation region defined by the vertically extending wall and at least a portion of the top core.

10. A centrifuge bowl according to claim 9, wherein the primary separation region is fluidly connected to the separation region.

11. A centrifuge bowl according to claim 9, further comprising a fluid pathway fluidly connecting the inlet tube and the primary separation region.

12. A centrifuge bowl according to claim 11, wherein the fluid pathway extends between a bottom wall of the top core and an upper surface of the bottom core.

13. A centrifuge bowl according to claim 1, wherein the inlet tube and first blood component extraction tube extend through the chimney.

14. A centrifuge bowl according to claim 13, further comprising a bypass seal between an outer diameter of the inlet tube and an inner diameter of the chimney, the bypass seal isolating the introduction region from the chimney.

15. A centrifuge bowl according to claim 14, wherein the bypass seal is a rotary seal.

16. A centrifuge bowl according to claim 1, further comprising a weir disk extending inward from the neck portion of the outer body, the second blood component flowing over the weir disk into the neck portion of the outer body prior to exiting the centrifuge bowl via the second blood component outlet port.

17. A centrifuge bowl according to claim 16, further comprising a second blood component channel defined by a bottom surface of the weir disk and a top surface of the top core, the second blood component channel fluidly connecting the secondary separation region and the second blood component outlet port.

* * * * *